United States Patent
Sutton et al.

(10) Patent No.: US 6,204,054 B1
(45) Date of Patent: Mar. 20, 2001

(54) TRANSCYTOSIS VEHICLES AND ENCHANCERS FOR DRUG DELIVERY

(75) Inventors: Andrew Derek Sutton, Grantham (GB); Asrar Bari Malik; Chinnaswamy Tiruppathi, both of Chicago, IL (US); Richard Alan Johnson, Nottingham (GB)

(73) Assignee: Andaris Limited (GB)

( * ) Notice: Subject to any disclaimer, the term of this patent is extended or adjusted under 35 U.S.C. 154(b) by 0 days.

(21) Appl. No.: 09/043,412
(22) PCT Filed: Sep. 20, 1996
(86) PCT No.: PCT/GB96/02326
   § 371 Date: Jun. 25, 1998
   § 102(e) Date: Jun. 25, 1998
(87) PCT Pub. No.: WO97/10850
   PCT Pub. Date: Mar. 27, 1997

Related U.S. Application Data
(60) Provisional application No. 60/004,097, filed on Sep. 21, 1995.

(30) Foreign Application Priority Data
Mar. 26, 1996 (GB) .................................... 9606315

(51) Int. Cl.[7] .............................. C12N 5/06; C12N 5/08; A61K 39/395; A61L 15/16
(52) U.S. Cl. ...................... 435/334; 435/371; 424/143.1; 424/158.1; 424/447
(58) Field of Search ................................... 435/334, 371; 424/447, 143.1, 158.1

(56) References Cited

U.S. PATENT DOCUMENTS 5,254,342  10/1993  Shen et al. ........................... 424/401

FOREIGN PATENT DOCUMENTS

WO 88/00834  2/1988  (WO) .
WO 93/20834  10/1993  (WO) .

OTHER PUBLICATIONS

Ghitescu, L. et al., "Specific Binding Sites for Albumin Restricted to Plasmalemmal Vesicles of Continuous Capillary Endothelium: Receptor–mediated Transcytosis," *J. Cell. Biol.* 102:1304–1311 (1986).

Schnitzer, J. E., "gp60 is an albumin–binding glycoprotein expressed by continuous endothelium involved in albumin transcytosis," *Am. J. Physiol.* 262 (*Heart Circ. Physiol.* 31*)*:H246–H254 (1992).

Schnitzer, J. E. and Oh, P., "Antibodies to SPARC inhibit albumin binding to SPARC, gp60, and microvascular endothelium," *Am. J. Physiol.* 263 (*Heart Circ. Physiol.* 32*)*:H1872–H1879 (1992).

Schnitzer, J. E. and Oh, P., "Albondin–mediated capillary permeability to albumin. Differential role of receptors in endothelial transcytosis and endocytosis of native and modified albumins,"*J. Biol. Chem.* 269:6072–6082 (Feb. 1994). Database Medline, Accession No. 94164970 (Abstract).

*Primary Examiner*—Hankyel T. Park
(74) *Attorney, Agent, or Firm*—Saliwanchik, Lloyd & Saliwanchik

(57) ABSTRACT

Transcytosis of a physiologically-active agent that exerts its action following passage across endothelia, epithelia or mesothelia containing the GP60 receptor is enhanced by formulation with or conjugation to a transcytosis enhancer or vehicle selected from albumin and fragments thereof, anti-GP60 antibody and fragments thereof, GP60 peptide fragments, and PDI (protein disulphide isomerase) and fragments thereof.

15 Claims, No Drawings

TRANSCYTOSIS VEHICLES AND ENCHANCERS FOR DRUG DELIVERY

CROSS-REFERENCE TO RELATED APPLICATION

This application is a U.S. national phase application corresponding to International Patent Application No. PCT/GB96/02326, filed Sep. 20, 1996 (pending).

This application claim benefit to provisional application Ser. No. 60/004,097 Sep. 21, 1995.

FIELD OF THE INVENTION

The invention relates to drug delivery. In particular, the invention relates to transcytosis vehicles and enhancers capable of delivering and enhancing passage of drugs across endothelia, epithelia and mesothelia containing the GP60 receptor.

BACKGROUND OF THE INVENTION

For most therapeutic drugs administered by intra-arterial or intravenous routes the intended site of molecular activity lies outside the vasculature. For drugs administered via the airways, the intended site of activity normally is beyond the first cellular barrier of alveolar, bronchiolar or tracheal epithelia. In both cases, there is an endothelial or epithelial barrier which must be crossed before the drug can mediate its effect.

For small lipophilic drugs, there appears to be a paracellular route between the tight junctions of the barrier cells. However, for hydrophilic drugs and larger macromolecular active agents, such as peptides, proteins, genes or anti-sense nucleotides, the only route across the barrier is through the cells. This poses a particular problem for drugs administered intravenously which have exceedingly short half-lives due to rapid degradation or first pass clearance by the liver. In order to maintain therapeutic levels in balance with such excretion and degradation, large doses or infusions are often necessary. Thus, there is clearly a need in the art for more rapid mechanisms for delivering drugs across cellular barriers.

There have been numerous reports of specific receptors which mediate endocytotic events, where a ligand binds to the receptor and is then internalized, complexed to the receptor, by a process similar to pinocytosis. This involves invagination of the cell membrane in the region of the ligand receptor complex and then release of the ligand into the cell by a process which is not fully understood. Numerous endocytotic receptor systems have been reported including LDL, insulin, epidermal growth factor, insulin-like growth factor and tPA-PAI-I (hybrid molecule).

Transcytosis entails invagination and vesicle formation around a ligand receptor complex, followed by transcytotic passage with release by a reverse invagination process at the basolateral membrane. Monoclonal antibodies to the transferrin receptor have been conjugated with toxins, so that they can undergo transcytosis, across blood-brain endothelia. However, there is a continuing need in the art for agents capable of delivering or enhancing passage of drugs by receptor-mediated transcytosis across cellular barriers other than blood-brain endothelia, such as endothelia of the vasculature, alveolar epithelia, and peritoneal mesothelia.

The GP60 receptor, also referred to as albondin, is one of several albumin-binding proteins reported in the literature (Schnitzer and Oh, J. Biol. Chem. 269(8):6072–6082 (1994)). Others include SPARC (serum protein, acidic, rich in cysteine), oesteonectin or basement membrane protein 40, GP30, GP18 and GP60. SPARC and oesteonectin are extracellular proteins. GP60 shares some homology with SPARC as determined using anti-SPARC antibodies (Schnitzer and Oh, Am. J. Physiol. 263:H1872–H1879 (1992)).

GP18 and GP30 are membrane glycoproteins found in a variety of cell types but are particularly prevalent in the macrophage (Schnitzer et al, J. Biol. Chem. 267: 24544–24553 (1992)). GP18 and GP30 are the so-called "scavenger receptors" responsible for mediating removal of oxidized, glycated or adduced forms of albumin by endocytosis and are thus believed to play a role in albumin catabolism for a wide variety of organs (Schnitzer and Bravo, J. Biol. Chem. 268(10):7562–7570 (1993)).

In contrast to GP18 and GP30, the GP60 receptor has found to be expressed exclusively in continuous endothelia of the vasculature (Schnitzer, Am. J. Physiol. 262:H246–H254 (1992)), in alveolar epithelia (Kim et al, Am. J. Resp. and Crit. Care Med. 151:A190, (1994) and inferentially in peritoneal mesothelia (Gotloib and Shostak, Kidney International. 47:1274–1284 (1995)). GP60 is particularly abundant in the microvessel endothelia and is, interestingly, absent from the blood-brain barrier, where little albumin flux is observed (Rousseaux et al, Methods in Enzymology 121:163 (1986)). It has been shown that polyclonal antibodies to endothelial GP60 also bind alveolar epithelial GP60 (Kim et al, supra). The GP60 receptor has been implicated in receptor-mediated transcytosis of albumin across epithelia and endothelial cell barriers (Kim et al, supra; Tirrupathi et al, Molecular Biology of the Cell 4 (Supp):338a, Abstract No. 1964 (1993)).

The GP60 amino acid sequence is known in the art (Yamauchi et al, Biochem. Biophys. Res. Comm. 146:1485 (1987)).

SUMMARY OF THE INVENTION

The present invention provides transcytosis vehicles and enhancers capable of transporting physiologically-active agents across epithelia, endothelia and mesothelia containing the GP60 receptor. The GP60 receptor has been implicated in receptor-mediated transcytosis of albumin across cell barriers. By means of the invention, GP60 receptor-mediated transcytosis can be exploited for the transport of not only albumin, but also physiologically-active agents which do not naturally pass through epithelia, endothelia and mesothelia via the GP60 system.

Transcytosis vehicles and enhancers of the invention include albumin, albumin fragments, anti-GP60 polyclonal and monoclonal antibodies, anti-GP60 polyclonal and monoclonal antibody fragments, and GP60 peptide fragments. Further, they include PDI (protein disulphide isomerase) and fragments thereof (any subsequent reference to GP60 fragments may be interpreted as referring also to PDI fragments). A common factor may be a CGMC motif found in PDI and at least the $T_{1-44}$ fragment of GP60. If the transcytosis vehicle or enhancer is a GP60 peptide fragment, it is preferably co-administered with other transcytosis vehicles or enhancers of the present invention such as albumin or an albumin fragment. Suitable albumin fragments of 14, 20 and 32 kDa can be generated by cleavage at methionine residues using cyanogen bromide and can be further reduced in size by reduction of disulfide bridges. Anti-GP60 polyclonal and monoclonal antibody fragments useful as transcytosis vehicles and enhancers according to the present invention include Fab, Fab', F(ab')$_2$, and Fv fragments. Preferred GP60 peptide fragments include the T3118 peptide which corresponds to the N-terminal 18 amino acids of the GP60 protein.

In accordance with the invention, when the above compounds are conjugated to a physiologically-active agent, they are referred to herein as "transcytosis vehicles". When co-administered with but not conjugated to a physiologically-active agent, the above compounds are referred to herein as "transcytosis enhancers". In preferred embodiments, the transcytosis vehicles and enhancers of the present invention are useful for delivering or enhancing passage of physiologically-active agents across endothelia of the vasculature, alveolar epithelia and peritoneal mesothelia.

DETAILED DESCRIPTION OF THE INVENTION

As its name indicates, the GP60 protein has been reported in the art as having a molecular weight of about 60 kDa. After a more careful analysis, it has been discovered that the "true" molecular weight for this protein is more probably about 57 kDa. This discrepancy in molecular weight is thought to be due to differences in protein preparation and gel conditions. However, to be consistent with the art, this protein is referred to herein (with the exception of Example 1 below) as the GP60 receptor.

It has been discovered that GP60 receptor-mediated transcytosis can be exploited for the transport of not only albumin, but also for a vast number of therapeutically-important physiologically-active agents which do not naturally pass through epithelia, endothelia and mesothelia via the GP60 system. Thus, the present invention provides an improved method for transporting physiologically-active e.g. those having relatively high molecular weights, e.g. 50, 100, 150 kDa or more, across the cellular barriers of the endothelia of the vasculature, alveolar, bronchiolar, and tracheal epithelia, and the peritoneal mesothelia. Transcytosis vehicles and enhancers capable of delivering or enhancing passage of physiologically-active agents across GP60-containing endothelia, epithelia and mesothelia include albumin, albumin fragments, anti-GP60 polyclonal and monoclonal antibodies, anti-GP60 polyclonal and monoclonal antibody fragments, and GP60 peptide fragments. If the transcytosis vehicle or enhancer is a GP60 peptide fragment, it will preferably be co-administered with other transcytosis vehicles or enhancers of the present invention such as albumin or an albumin fragment.

Mammalian albumin is well known in the art and readily available. Preferably, the albumin used will be from the same mammalian species as the patient. For example, if the patient is human, human serum albumin will preferably be used as the transcytosis vehicle or enhancer. Similarly, if the patient is equine or bovine, equine or bovine serum albumin is preferably used, respectively.

Methods for generating albumin fragments are well known in the art. For example, cleavage of albumin at methionine residues by cyanogen bromide yields three particularly suitable peptides of 14, 20 and 32 kDa which can be further reduced in size by reduction of the disulfide bridges, to peptides ranging in size from 3.3–20 kDa. Alternatively, protease digestion can be used to generate albumin peptide fragments.

Whether any particular albumin fragment is useful as a transcytosis vehicle or enhancer according to the present invention can be determined according to the routine screening assay described below. As indicated in the Examples below, it has now been demonstrated that both bovine and human serum albumin, acting as transcytosis enhancers, stimulate uptake of a physiologically-active agent 2.5–4 fold over the control.

Anti-GP60 polyclonal and monoclonal antibodies can be generated from the GP60 receptor purified from endothelia, epithelia or mesothelia. As discussed above, endothelial, epithelial and mesothelial cells which express the GP60 receptor include endothelia of the vasculature (including capillary endothelia (Ghinea et al, J. Cell Biol. 107:231–239 (1988)); arterial endothelia (Silflinger-Birnboim et al, J. Cellular Physiology 149:575–584 (1991); aortic and vein endothelia (Schnitzer and Oh, Am. J. Physiol. (1992), supra); epithelia of alveolar tissue (Kim et al, supra); and mesothelia of the peritoneum (Gotloib and Shostak, supra). GP60 can be purified from epithelia, endothelia and mesothelia according to art-known methods (see, for example, Schnitzer and Oh, J. Biol. Chem. (1994), supra) and as described in Example 1 below.

Producing polyclonal antibodies against purified GP60 or a GP60 peptide fragment (such as the T3118 peptide discussed below) can occur in mice, rabbits, or goats according to art-known techniques. In Example 1 below, the GP60 receptor was eluted from preparative SDS-PAGE to immunize rabbits. Approximately 50 µg protein per rabbit was injected intramuscularly after mixing with equal volume of Freund's complete adjuvant. A second injection was given after two weeks. Rabbits were bled at 4 to 6 weeks after the second injection, and the immune response was tested. The antiserum IgG was then purified using a Protein A-Sepharose column.

Monoclonal antibody preparation can also occur according to known techniques (Goding, J. Immunol. Methods 39:285 (1980); Oi and Herzenberg, Selected Methods in Cellular Immunology, p. 352, Freeman, San Francisco, 1979)). For example, Balb/c mice are injected intraperitoneally with 50–150 µg of GP60 or a GP60 peptide fragment. Three to five days before the fusion, positive mice receive a booster injection of antigen (50–150 µg of GP60 or GP60 fragment), and then 10 µg (intravenous and intraperitoneal route) every day until spleen removal. The spleen cells are fused with Sp2/0-Ag14 myeloma cells essentially according to St. Groth et al, J. Immunology Methods 35:1–21 (1980). Culture supernatants are screened by ELISA using unconjugated GP60 or GP60 fragment as antigen. Positive cultures are then tested by immunofluorescence and Western blotting on cDNA-transfected COS-1 cells as described in Lutz et al, Experimental Cell Research 175:109–124 (1988). Hybridomas secreting specific antibodies are cloned twice on soft agar. Each hybridoma can be adapted in serum-free medium SFRI-4. For ascites fluid production, approximately 2×106 cells are injected in pristine-primed Balb/c mice. Class and subclass determination is performed using an Isotyping Kit. Both SFRI culture supernatants and ascites fluids can be used as monoclonal antibody sources.

As discussed, the anti-GP60 polyclonal and monoclonal antibodies and antibody fragments of the present invention are useful as transcytosis vehicles and enhancers capable of delivering or enhancing passage of physiologically-active agents across endothelia, epithelia and mesothelia containing the GP60 receptor. Anti-GP60 antibody fragments useful as transcytosis vehicles or enhancers of the present invention include fragments containing single (Fab) antigen binding domains produced by papain digestion; or F(ab')$_2$ fragments produced by limited pepsin digestion (Olsson and Kaplan, Methods in Enzymology 92:3 (1983)). Other suitable fragments include Fab' and Fv. Whether any particular antibody fragment is useful as a transcytosis vehicle or enhancer can be determined according to the routine screening assay described below. In Example 3 below, it is demonstrated that administering anti-GP60 polyclonal antibodies at 37° C.

results in a 1.6–2 fold increase in uptake of a physiologically-active agent over the level of a pre-immune serum control.

According to the invention, anti-GP60 antibodies raised in animals other than humans such as mice and rats are suitable for short-term administration only (i.e., non-chronic dosage) due to the well-known adverse immune response to foreign antibodies. However, art-described methods can be used to produce human monoclonal antibodies to the GP60 receptor, to overcome the problems of administering murine monoclonals to humans (Olsson and Kaplan supra), thereby rendering the antibodies suitable for long-term or chronic administration. Moreover, the murine antibodies of the present invention can be "humanized" by chimeric or CDR grafting. The recognition region of the murine antibody is grafted into the appropriate region of a human antibody, in order to avoid or limit an adverse immune response in a patient.

GP60 peptide fragments are also useful as transcytosis vehicles and enhancers according to the present invention. Particularly suitable GP60 peptide fragments include the first 18 amino acids from the N-terminus of GP60; it has been discovered that this is at least 80% homologous to a stretch of the bovine, membrane-bound thyroid hormone (T3) binding protein. Such GP60 peptide fragments can be produced according to any known enzymatic or physical technique, including proteolytic degradation. Alternatively, GP60 peptide fragments can be produced synthetically. As indicated in Example 5 below, a synthetic N-terminal peptide (T3118) of GP60 corresponding to the first 18 residues may be produced by solid-phase synthesis. This peptide, acting as an agonist of transcytosis, stimulated uptake of human albumin 5-fold over the control.

Methods for conjugating the transcytosis vehicles of the present invention to a physiologically-active agent will be readily apparent to the skilled artisan and include, but are not limited to, glutaraldehyde conjugation involving Schiff base formation; carbodiimide reaction between proteins and carboxylic acids; acid anhydride activation of amine-containing drugs followed by carbodiimide linkage; activation of primary amine-containing drugs with 3-(2-pyridyldithio) propionate-N-succinimidyl anhydride followed by coupling to cysteine groups of proteins; coupling of sugar alcohols to proteins utilizing cyanuric chloride; and conjugation between amines and hydroxyl groups via bisperoxidation.

For example, the amino sugar moiety of a physiologically-active agent can be oxidized by sodium periodate treatment and directly attached to lysine residues on a transcytosis vehicle of the present invention via Schiff base formation according to the method described in Hurwitz et al, Cancer Res. 35:1175–1181 (1975). Alternatively, a physiologically-active agent can be linked to a transcytosis vehicle of the present invention through carbodiimide-mediated linkage of the amino group of the active to carbonyl groups on the vehicle or to an aminoalkyl group according to the method described in Hurwitz et al, Int. J. Cancer 21:747–755 (1978). The physiologically-active agent can also be linked to a transcytosis vehicle of the present invention by cross-linking the amino sugar of the active and amino groups of the vehicle with glutaraldehyde according to the method described in Belles-Isles et al, Br. J. Cancer 41:841–842 (1980).

Other suitable conjugation sites for conjugating physiologically-active agents to one of the transcytosis vehicles of the present invention can be routinely determined empirically. For example, a transcytosis vehicle of the present invention can be labelled with fluorescein or $^{125}I$ either before or after conjugation to a physiologically-active agent such as insulin. After conjugation and labelling, a screening assay such as that described in the Examples below can be used to determine the endothelial cell uptake, the epithelial cell flux, or the mesothelial cell flux of any candidate vehicle/active conjugate. Such a routine screening assay allows the skilled artisan to determine which transcytosis vehicles of the present invention retain the ability to undergo transcytosis after being conjugated at a particular site to a physiologically-active agent. Such an assay is also useful for routine screening of candidate albumin fragments, anti-GP60 antibody fragments and GP60 peptide fragments to determine which are suitable (for use as transcytosis vehicles and enhancers according to the present invention.

The conjugation of physiologically-active agents to a transcytosis vehicle of the present invention is particularly suited for intravenous delivery of low molecular weight drugs which otherwise have exceedingly short serum half-lives, or of peptide drugs that are rapidly degraded in the blood stream or removed by first pass excretion in the liver. Of course, where the physiologically-active agent is covalently conjugated to one of the transcytosis vehicles of the present invention, the residual activity of the therapeutic agent must be assessed after conjugation. Techniques for assaying a therapeutic agent's activity are well established in the art, and many therapeutics have successfully been conjugated and retained substantial activity. For example, the literature describes conjugates between receptor ligands, or fragments thereof, and drugs to promote transcytosis across the blood brain barriers. Fukta et al, Pharm. Research 11(12):1681 (1994), describe conjugation of horse radish peroxidase (HRP) to insulin which enabled HRP to cross the blood, brain barrier. The investigators went on to produce fragments of insulin which were screened for their ability to bind to the insulin receptor on bovine brain microvessel endothelial cells in culture. Similarly, other transcytosis systems allow the passage of antibodies linked with active drugs including, among others, antibody-methotrexate targeted to the transferrin receptor (Friden et al, Proc. Natl. Acad. Sci. USA 88:4771 (1991)), and antibody-polylysine targeted to the epidermal growth factor receptor (Chen et al, FEBS Lett. 338:167 (1994)).

By contrast to the transcytosis vehicles, transcytosis enhancers of the invention are not conjugated to the physiologically-active agent. It has been discovered that co-residence on epithelia, endothelia and mesothelia containing the GP60 receptor of one of the transcytosis enhancers of the present invention and a physiologically-active agent is sufficient to enhance uptake and passage of the agent across the cell barrier. Without wishing to be bound by theory, the transcytosis enhancers of the present invention apparently "trigger" the GP60-mediated transcytosis mechanism, thereby stimulating the enhanced uptake of co-resident macromolecules, including therapeutic agents.

Uptake or passage of physiologically-active agents by or across epithelia, endothelia and mesothelia can be induced or enhanced with any of the transcytosis enhancers of the present invention either alone or in combination. For example, the experiments below demonstrate that, acting as an agonist of transcytosis, the GP60 peptide T3118 enhanced human albumin uptake 5-fold over the control. In a further embodiment of the present invention, delivery of active agents can be achieved when one of the transcytosis vehicle conjugates discussed above is administered together with one or more of the transcytosis enhancers of the present invention.

The transcytosis vehicle conjugates and the transcytosis enhancer compositions (including an active agent) of the present invention can be administered with a pharmaceutically-acceptable carrier or excipient, i.e., pharmaceutically-acceptable organic or inorganic substances suitable for application which do not deleteriously react with the conjugate or composition. Suitable pharmaceutically-acceptable substances include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, colourings, flavouring and/or aromatic substances, which do not deleteriously react with the conjugates. For parenteral application, particularly suitable preparations are solutions, preferably oily or aqueous solutions, as well as suspensions, emulsions, or implants, including suppositories. Ampoules are convenient unit dosages. For enteral application, particularly suitable preparations are tablets, dragees or capsules having a carrier binder such as talc and/or a carbohydrate, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Administration of a conjugate or composition comprising one or more physiologically-active agents and one or more of the transcytosis vehicles or enhancers of the present invention can occur according to any art-known technique including injection or via the pulmonary airways. Injection is particularly suitable for administration to the vasculature and the peritoneum, whereas the pulmonary airways are particularly suitable for administration to the alveoli. Suitable formulations for pulmonary administration include one or more of the transcytosis enhancers of the present invention admixed with a physiologically-active agent. Alternative suitable formulations for pulmonary administration include a transcytosis vehicle conjugated to the agent. For example, formulations may be made from a nebulizer device such as an Acorn or DeVilbiss jet nebulizer, wherein the agent and transcytosis enhancer or vehicle are presented as an aqueous solution in the nebulizer reservoir. Alternatively, in a preferred embodiment for pulmonary administration, the formulation is discharged from a dry powder inhaler (DPI) device. DPI devices are described by Sutton et al in U.S. patent application Ser. No. 08/487,420 and in WO-9609814. They require spray-drying the formulation into microparticles of 2–5 $\mu$m which are preferred for alveolar penetration.

In particular, a transcytosis enhancer or vehicle of the present invention or a mixture thereof, preferably at a concentration of about 20% w/v, is used for spray-drying. The preparation to be sprayed may contain substances other than the transcytosis enhancers or vehicles and solvent or carrier liquid. For example, the aqueous phase may contain 1–20% by weight of water-soluble hydrophilic compounds such as sugars and polymers as stabilizers, e.g., polyvinyl alcohol (PVA), polyvinyl pyrrolidone (PVP), polyethylene glycol (PEG), gelatin, polyglutamic acid and polysaccharides such as starch, dextran, agar, xanthin and the like. Similar aqueous phases can be used as the carrier liquid in which the final microsphere product is suspended before use. Emulsifiers may be used (0.1–5% by weight), including most physiologically-acceptable emulsifiers, for instance egg lecithin or soya bean lecithin, or synthetic lecithins such as saturated synthetic lecithins, for example, dimyristoyl phosphatidylcholine, dipalmitoyl phosphatidylcholine, or distearoyl phosphatidylcholine or unsaturated synthetic lecithins, such as dioleyl phosphatidylcholine or dilinoleyl phosphatidylcholine. Emulsifiers also include surfactants such as free fatty acids, esters of fatty acids with polyoxyalkylene compounds, e.g. polyoxypropylene glycol and polyoxyethylene glycol; ethers of fatty alcohols with polyoxyalkylene glycols; esters of fatty acids with polyoxyalkylated sorbitan; soaps; glycerol-polyoxyethylene ricinoleate; homo-and copolymers of polyalkylene glycols; polyethoxylated soya-oil and castor oil as well as hydrogenated derivative; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose.

Additives can be incorporated into the wall of the microspheres to modify the physical properties such as dispersibility, elasticity and water permeability. Among the useful additives include compounds which can "hydrophobize" the wall in order to decrease water permeability, such as fats, waxes and high molecular weight hydrocarbons. Additives which improve dispersibility of the microspheres in the injectable liquid-carrier are amphipathic compounds such as phospholipids; they also increase water permeability and rate of biodegradability. Additives which increase wall elasticity include plasticizers such as isopropyl myristate and the like. The quantity of additives to be incorporated in the wall is extremely variable and depends on the needs. In some applications, no additive is used at all; in other cases, amounts of additives which may reach about 20% by weight of the wall are possible.

A solution containing one or more transcytosis enhancers or vehicles of the present invention and additive, if any, is atomized and spray-dried by any suitable technique which results in discrete microspheres or microcapsules of 2 to 5 $\mu$m as discussed above. As used herein, "microcapsules" refers to hollow particles enclosing a space, which space is filled with a gas or vapour but not with any solid materials.

The atomization forms an aerosol of the transcytosis vehicle or enhancer formulation, for example by forcing the formulation through at least one orifice under pressure, or by using a centrifugal atomizer in a chamber of warm air or other inert gas. The chamber should be big enough for the largest ejected drops not to strike the walls before drying. The gas or vapour in the chamber is clean (preferably sterile and pyrogen-free) and non-toxic when administered to the bloodstream in amounts concomitant with administration of the microcapsules in use. The rate of evaporation of the liquid from the preparation should be sufficiently high to form hollow microcapsules but not so high as to burst the microcapsules. The rate of evaporation may be controlled by varying the gas flow rate, concentration of transcytosis vehicle or enhancer in the formulation, nature of liquid carrier, feed rate of the solution and, more importantly, the temperature of the gas encountered by the aerosol. For example, an albumin or albumin fragment concentration of 15–25% in water, and an inlet gas temperature of at least about 100° C., preferably at least 110° C., is sufficient to ensure hollowness and the temperature may be as high as 250° C. without the capsule bursting. About 180–240° C., preferably about 210–230° C. and most preferably about 220° C., is optimal. Since the temperature of the gas encountered by the aerosol will depend also on the rate at which the aerosol is delivered and on the liquid content of the preparation, the outlet temperature may be monitored to ensure an adequate temperature in the chamber. An outlet temperature of 40–150° C. is suitable. Controlling the flow rate is useful in controlling other parameters such as the number of intact hollow particles.

The microparticles may comprise at least 50%, more preferably 70% or 80%, and most preferably 90%, by weight transcytosis enhancer. For use in an inhaler device, the microparticles may be formulated with a conventional excipient such as lactose or glucose. The amount of the physiologically-active agent will be chosen with regard to its nature and activity, to the mode of administration and other factors known to those of skill in the art. By way of example, the number of particles administered may be such as to deliver 100 mg/day α-1 anti-trypsin, or 0.1 mg/day of an active agent such as beclomethasone. Other possible physiologically-active agents that can be administered via microparticles are given below.

A further embodiment of the present invention is the co-spray-drying of the physiologically-active agent with the transcytosis enhancer in order to facilitate stabilization of the active agent during formulation, packing, and most importantly, during residence on the alveolar lining. In this environment, there can be intense proteolytic activity. In this or another embodiment, the active agent may be covalently linked to the transcytosis vehicle via cleavable linkages prior to spray-drying. This embodiment represents a method of carrying the active agent all the way from the device to the bloodstream, and possibly to targets within the body. The formation of particles with optimal aerodynamic size means that the "physical" vehicle delivers the active agent to the site of absorption. Once deposited upon the alveoli, the "molecular" vehicle then protects and facilitates passage into the bloodstream via the GP60-mediated transcytosis system and, once in the bloodstream, can further enhance circulatory half-life and even direct the active agent to certain sites which are found to contain the GP60 receptor. Suitable linking technologies are discussed above; further, WO-A-9317713 describes esterase-sensitive polyhydroxy acid linkers. Such technology, used in the derivatization of the transcytosis vehicle prior to spray-drying, enables the production of a covalent carrier system for delivery of active agents to the systemic vasculature. This utilizes the potential of the transcytosis vehicles to cross the alveoli and to carry active agents over a prolonged period while protecting potentially unstable entities.

Although the physiologically-active agent used in the present invention my be imbibed into or otherwise associated with the microparticles after their formulation, it is preferably formulated with the transcytosis vehicle or enhancer. The microparticles may be at least partly coated with a hydrophobic or water-insoluble material such as a fatty acid, in order to delay their rate of dissolution and to protect against hydroscopic growth.

Methods and equipment for spray-drying and generating the microparticles, e.g. for use in a dry powder inhaler device are described in more detail in WO-A-9609814 and in U.S. patent application Ser. No. 08/487,420, the contents of which are incorporated herein by reference.

The optimal proportions of drug to transcytosis enhancer in a formulation for pulmonary delivery can be determined according to any suitable method. An in vitro optimization of the formulation entails using epithelial monolayers of primary human or immortalized human epithelial cells grown as monolayers on porous filters, as described in the Examples below. Combinations of drug and enhancer may then be applied to the upper chamber of a transwell flux system also as described below. Using either labelled tracer or an immunoassay, flux rates of the drug or gene to the lower layer are determined. The optimal formulation is defined as the one showing maximal rate and extent of passage through the restrictive monolayer.

An alternative way of optimizing the formulation entails performing an in vivo determination of lung to blood passage of the drug under investigation. There are well-reported studies in rat, pig and sheep (Patton et al, Journal of Controlled Release 28:79 (1994), Folkesson et al, Acta. Physiol. Scand. 147:73 (1993); Schreier et al, Pharm. Res. 11:1056 (1994)); these studies describe methods of instilling or aerosolizing drug formulations into the trachea and bronchioles and assessing the appearance in blood of the drug by immunoassay or pharmacological activity. Optimization would entail a series of animal preparations using differing proportions of the drug and enhancer, the optimal formulation being defined by the most beneficial area under the curve that matched the desired pharmacological profile for the drug. For instance, the drug may simply be required to show the maximal bioavailability or alternatively to show a protracted or sustained release profile. For each case, it is likely that there would be differing requirements for the level of enhancer incorporated in the formulation. For drugs requiring maximal availability, it would be desirable to utilize the maximal level of enhancer and/or the enhancer showing the highest activating effect upon the GP60 receptor. For drugs requiring a longer period of presentation across the lung, it would be desirable to utilize lower levels of enhancer and/or enhancers showing lower activation potential on the transcytosis GP60 receptor.

The "strength" of the enhancer or vehicle can be defined, by the extent to which transcytosis of a given tracer can be enhanced, by the presence of the GP60 receptor-binding ligand, antibody or mimetic, over the level of transcytosis in the absence of the ligand. The "strength" of the enhancing agent may be somewhat drug-dependent also. Enhancement of marker uptake can vary dependent upon the nature of the marker and the transcytosis enhancer. Tabulated below is a synopsis of the markers, enhancers, cell system and extent of enhancement over the control achieved for differing markers cell systems and experimental type.

Abbreviations used:

| | |
|---|---|
| $^{125}$I-BSA | $^{125}$Iodine-labelled bovine albumin |
| $^{125}$I-IgG | $^{125}$Iodine-labelled Immunoglobulin G |
| HSA | Human albumin |
| BSA | Bovine albumin |
| FITC-Insulin | fluorescein-labelled insulin |
| GP60 Ab | Anti-GP60 polyclonal antibody |
| T3118 | Synthetic peptide derived from N terminal 18 residues of GP60 |

| Marker | Enhancer | Cell Type | Fold Enhancement |
|---|---|---|---|
| $^{125}$I-BSA | GP60 Ab | Bovine/Endothelia/flux | 1.6 |
| $^{125}$I-BSA | GP60 Ab | Bovine/Endothelia/flux | 2.0 |
| anti-BSA $^{125}$I-IgG | BSA | Bovine/Endothelia/flux | 1.5 |
| FITC-Insulin | HSA | Human Endothelia/flux | 2.5 |

-continued

| | | | |
|---|---|---|---|
| FITC-Insulin | BSA | Rat Epithelia/flux | 4 |
| $^{125}$I-BSA | BSA/T3118 | Bovine Endothelia/uptake | 5 |

By "physiologically-active agent" is intended drugs which include nucleic acid molecules and medicinal peptides and proteins. "Physiologically-active agent" is used interchangeably herein with "drug", "active", "active agent" and "therapeutic". Drugs that would benefit from a more rapid transcytosis across the endothelia and epithelia include Luteinizing hormone (LH), chorionic gonadotropin, atrial peptides, interferon, the various lymphokines such as the interleukins (I, II, III, IV, V, VI, and VII), and colony-stimulating factors.

Other drugs suitable for use in the present invention include: Growth hormone-releasing factor, corticotropin-releasing factor, luteinizing hormone-releasing hormone (LHRH), somatostatin, calcitonin, thyrotropin-releasing hormone, calcitonin gene-related peptide (CGRP), proteins such as enzymes, including transferases, hydrolases, isomerases, proteases, ligases, oxidoreductases, esterases and phosphatases, and various growth and neurotrophic factors, such as somatomedins, epidermal growth factors, urogastrone, nerve growth factor (NGF), ciliary neurotrophic factor (CNTF), brain-derived neurotrophic factor (BDNF), glial-derived neurotrophic factor (GDNF), epidermal growth factor (EGF), fibroblast growth factor (FGF), insulin-like growth factor, tumour necrosis factor (TNF) and transforming growth factor (TGF). Further drugs include endogenous opioid agonists, such as encephalins and endorphins; hypothalamic hormones, such as gonadoliberin, melanostatin, melonoliberin, somatostatin, thyroliberin, substance P, and neurotensin; adenohypophyseal hormones, such as corticotropin, lipotropin, melanotropin, lutropin, thyrotropin, prolactin, and somatotropin; neurohypophyseal hormones; calcitrapic (thyroid) hormones, such as parathyrin and calcitonin; thymic factors, such as thymosin, thymopoietin, circulating thymic factor, and thymic humoral factor; pancreatic hormones, such as insulin, glucagon and somatostatin; gastrointestinal hormones, such as gastrin, cholecystokinin, secretin, gastric inhibitory polypeptide, vasointestinal peptide, and motillin; ovarian hormones, such as relaxin; vasoactive tissue hormones, such as angiotensin and bradykinin; and artificial or pseudo peptides, such as deferoxamine; and LHRH analogs such as buserelin, deslorelin, gonadorelin, goserelin, histrelin, leuprorelin, nafarelin, or triptorelin.

Having generally described the invention, the same will be more readily understood through reference to the following Examples which are provided by way of illustration but are not intended to be limiting.

EXAMPLE 1

Growth of Endothelial and Epithelial Monolayers

Bovine pulmonary microvessel endothelial cells (BPMVEC) and (BPAEC) bovine pulmonary artery endothelial cells were isolated and cultured according to described methods (Del Vecchio et al, In Vitro. Cell. Dev. Biol. 28A:711–715 (1992)). Endothelial cells were routinely cultured with DMEM containing 20% FBS. For isolating plasma membranes, the endothelial cells were cultured in 850 cm$^3$ roller bottles. To each roller bottle, 75 ml culture medium was added. An air-$CO_2$ mixture was introduced. The cells were then transferred to a roller bottle incubator at 37° C., and were allowed to grow for 10–12 days.

Primary rat alveolar epithelial cells (AEC) were isolated by methods described in Uhal et al, Am. J. Physiol. 257:C528–C536 (1989). Cells were cultured in DMEM containing 10% FBS for either 2 or 4 days, at which times they exhibited a type II or type I cell-like phenotype respectively. Phenotype was verified by methods described by Uhal et al, Am. J. Physiol. Suppl. 261:110–117 (1991).

Endothelial Cell Membrane Isolation

Endothelial cells grown in roller bottles were washed 2× with phosphate buffered saline. The cells were scraped from roller bottles and suspended in Buffer-A (20 mM HEPES/Tris, 0.15 M NaCl, 0.1 mM PMSF at pH 7.4) and washed 2× by centrifuging at 700×g for 10 minutes. The cells obtained from 6–8 roller bottles were suspended in 75 ml of buffer-A and homogenized using a Polytron homogenizer for 1 minute at full speed. The homogenate was centrifuged at 3000×g for 10 minutes. The supernatant was collected and centrifuged at 40,000×g for 60 minutes. The pellet obtained was then suspended in buffer-A and recentrifuged at 40,000×g for 60 minutes. The final membrane pellet was suspended in a small volume of buffer-A containing 0.2 mM EDTA and the protein concentration was determined (Lowry et al, J. Biol. Chem. 193:265–275 (1951)). The plasma membrane marker enzyme activities were determined and the sample stored at −70° C. until further use.

Ligand Blotting

Endothelial cell membranes were preincubated with 1 mM PMSF and 0.5 mM EDTA for 20 minutes at 22° C., and then solubilized by mixing with 1.5 volume of solubilizing buffer (9M urea, 2% SDS, 2% β-mercaptoethanol, 0.1 M Tris, 0.02% bromophenol blue pH 6.8). The mixture was incubated at 22° C. for 30 minutes. The solubilized proteins were separated by SDS-PAGE (Laemmli, Nature (London) 227:680–685 (1970)) using a slab-gel electrophoretic system with 3% acrylamide in the stacking gel and 10% acrylamide in the separating gel. After electrophoresis, the proteins were transferred to either PVDF or nitrocellulose membrane. The transfer was carried out for 2 hours at 150 volts using 25 mM Tris, 192 mM glycine, and 20% methanol as transfer buffer. The non-specific binding was blocked by incubating the membrane with 5 mM $CaCl_2$ in TBS (20 mM Tris, 0.5 M NaCl at pH 7.5) for 10 minutes and then with 0.5% Tween-20 in TBS overnight. After this step, the membrane was washed and cut into two strips. One strip was incubated with 0.6 mg/ml globulin-free BSA in TBS containing 1.5% gelatin for 2 hours and the other strip was incubated without BSA. The strips were washed and incubated with anti-bovine BSA for 60 minutes in TBS containing 1.5% gelatin. The membranes were then washed 2× and incubated with second antibody (goat anti-rabbit IgG) conjugated with alkaline phosphatase. The protein bands were localized after adding 5-bromo-4-chloro-3-indolylphosphate and nitroblue tetrazolium salt.

Protein Purification

BPMVEC membranes were used to isolate a 57 kDa albumin-binding protein. The ligand blotting was carried out to assess the presence of this protein in each step. BPMVEC membranes (100 mg) were preincubated with 1 mM PMSF and 0.5 mM EDTA for 30 minutes at 22° C. The membranes were solubilized using a final concentration of 2.5% sodium cholate and 4 M urea, at 4° C. for 3 hours, with gentle stirring. The protein concentration was adjusted to 4 mg/ml during solubilization. After this treatment, the suspension was centrifuged at 100,000×g for 60 minutes. The supernatant was collected and dialyzed against 5 mM HEPES/Tris (pH 7.2). More than 80% of membrane proteins were recovered in the supernatant. The dialysed suspension was concentrated by 60% ethanol precipitation at 4° C. The ethanol precipitate was collected by centrifugation at 10,000×g for 30 minutes at 4° C. and suspended in Buffer-A. This precipitate was solubilized with 2.5% Triton X-100 overnight at 4° C. with gentle stirring. The suspension was centrifuged at 100,000×g for 60 minutes. The supernatant was collected and dialysed against 4 l of 50 mM Tris-HCl, 0.2 mM EDTA, 0.15% Triton X-100 and 0.1 mM PMSF, pH 8.0 (Buffer-B). The dialysed extract was applied on a DEAE-52 column (10×13 cm). The column was previously equilibrated with Buffer-B. The column was washed with 50 ml of Buffer-B after applying the sample. The bound proteins were eluted from the column with 80 ml of 0–500 mM linear NaCl gradient in Buffer-B at a flow rate of 15 ml/hr. The fractions from individual peaks were pooled separately and concentrated by 50% acetone precipitation. The acetone precipitate was used for ligand blotting. Only peak-I showed albumin-binding activity. The proteins present in peak-I were further separated by using preparative SDS-PAGE (16 cm×16 cm, 3 mm thick slab-gel), and a 57 kDa protein eluted from the gel was used for further studies.

Antibody Production and Purification

The 57 kDa albumin-binding protein eluted from preparative SDS-PAGE was used to immunize rabbits. Approximately 50 $\mu$g protein (per rabbit) was injected intramuscularly after mixing with equal volume of Freund's complete adjuvant. A second injection was given after two weeks. Rabbits were bled at 4 to 6 weeks after the second injection and the immune response was checked. The preimmune serum IgG and the antiserum IgG were purified using protein A-sepharose column.

Immunoblotting

Endothelial cell membranes were subjected to SDS-PAGE (Laemmli, supra), and electrophoretically transferred to nitrocellulose or PVDF membrane. Non-specific binding was blocked with 3% gelatin in TBS for 5 hours at 22° C. The membrane was washed 2× with 0.5% Tween-20 in TBS and incubated with antiserum diluted in TBS containing 1% gelatin. The incubation was carried out for 4–6 hours, washed 2×, and then incubated for 60 minutes with the second antibody (goat anti-rabbit IgG coupled to alkaline phosphatase). After incubation, the membranes were washed 2× and the protein bands were localized as described under "Ligand Blotting". Molecular weights of the proteins were determined using known marker proteins.

Monolayer Binding Studies

BPMVEC were seeded (3×105 cells/well) in six well Corning tissue culture plates and grown to confluence. The monolayers were washed 2× with serum-free medium (20 mM HEPE/DMEM pH 7.4) and incubated with serum-free medium for 15–20 hours in a tissue culture incubator. After this incubation, the monolayers were washed 2× with binding buffer (20 mM HEPES/Tris HBSS pH 7.4) and the binding was initiated by adding 1 ml of 1 $\mu$M $^{125}$I-BSA in binding buffer. The incubation was carried out at 4° C. for 60 minutes. The binding was terminated by washing the monolayer 3× with the binding buffer. The radioactivity associated with the monolayer was determined after lysing the cells with 1 N NaOH (Tiruppathi et al, Am. J. Physiol. (Lung. Cell. Mol. Physiol.) L595–L601 (1992)). Non-specific binding was determined by the inclusion of unlabelled BSA (40 mg/ml) during the binding procedure. The test components, preimmune serum-IgG and the anti-57 kDa-IgG were preincubated for 30 minutes with the monolayer prior to the addition of $^{125}$I-BSA.

Trans-cellular Flux Experiments

Transendothelial $^{125}$I-albumin flux rates in cultured endothelial monoloyers were used to assess transendothelial albumin transport. The system used for this study has previously been described (Cooper et al, J. Appl. Physiol. 62:1076–1083 (1987); Garcia, et al, J. Cell. Physiol. 128:96–104 (1986); Del Vecchio, et al, Vitro. Cell. Dev. Biol. 28A:711–715 (1992) and Siflinger-Birnboirn et al, J. Cell. Physiol. 132:111–117 (1987)). The system measures the transendothelial movement of tracer macromolecules in the absence of hydrostatic and oncotic pressure gradients. It consists of luminal and abluminal compartments separated compartments separated by a polycarbonate microporous filter (0.8 $\mu$m pore diameter). BPMVEC were seeded at 105 cells/filter and grown for 3–4 days to attain confluency. Both compartments contained the same medium (20 mM HEPES-DMEM, pH 7.4) at volumes of 600 ml and 25 ml, respectively. The luminal compartment was fitted with a Styrofoam outer ring, and "floated" in the abluminal medium so that fluid levels remained equal after repeated samplings from the abluminal compartment. The abluminal compartment was stirred continuously and the entire system was kept at 37° C. by a thermostatically regulated water bath. Transendothelial clearance of $^{125}$I-albumin was determined as the volume of luminal chamber radioactivity cleared into the abluminal chamber. The change in volume over time provided the $^{125}$I-albumin clearance rate in $\mu$l/min as determined by weighted least-squares non-linear regression analysis (BMDP Statistical Software, Berkeley, Calif.).

At the beginning of the experiment, the luminal compartment was floated in the abluminal medium, and filled with medium containing about 6 $\mu$Ci/ml $^{125}$I-albumin. Abluminal samples, 400 $\mu$l, were collected at 10 minute intervals for up to 60 minutes and the radioactivity was measured using a gamma counter. At the end of the experiment, free $^{125}$I in the luminal and abluminal compartments was determined using 12% TCA precipitation and the transendothelial $^{125}$I-albumin flux rates were corrected for free $^{125}$I.

The day before the experiment, the BPMVEC monolayers were washed 2× with 20 mM HEPES-DMEM pH 7.4 (serum-free medium) and incubated at 37° C. in cell culture incubator with serum-free medium for 12–15 hours. After this incubation period, the test components (preimmune serum-IgG and the anti-57 kDA-IgG) were diluted in serum-free medium and incubated with the monolayers for the desired periods. These monolayers were then used for transendothelial albumin transport measurement.

Trans-epithelial flux rates were measured with slight modification to the method described for endothelial cells. Flux rates were determined on primary AEC or the A549 human lung carcinoma cell line cultured as described on Transwell filters (Costar) (Evans et al, Exper. Cell Res. 18:375–387 (1989)). Monolayer integrity is defined by transepithelial electrical resistance being greater than 500 ohms/cm$_2$. Filters with intact monolayers were placed in a 24 well culture plate containing 1 ml serum-free DMEM per well (abluminal chamber). The luminal chamber was filled with 200 $\mu$l serum-free DMEM containing the tracer molecule of interest (FITC-Insulin). The fluid levels in the two compartments were the same, eliminating hydrostatic pressure. The filter system was preincubated (30 mins) and then maintained at 37° C. in a $CO_2$ incubator throughout the flux experiment. At one and two hours, 300 $\mu$l samples were withdrawn from the abluminal chamber and immediately replaced with serum-free DMEM. The fluorescence of the transcytosed material was recorded on a plate reader, and the ratio of bound vs. free FITC determined by gel filtration chromatography of the abluminal samples.

Actin Filament Distribution

The actin filament distribution and cytoskeletal changes in endothelial monolayers grown on the filters were studied under the conditions identical to those used for the measurement of $^{125}$I-albumin clearance rates. After the required pretreatment period with the test components, the monolayers on the filter were fixed in 10% buffered formalin (Pallescences Inc., Warrington, Pa.), permeabilized with 1% Nonidet P40 (Sigma), and stained with rhodamine phalloidin (Molecular Probes, Inc., Eugene, Oreg.) as described by Phillips and Tsan, J. Histochem. Cytochem. 36:551–554 (1988). The intact filters containing the monolayers were removed from the wells and mounted on coverslips, covered with a 1:1 solution of glycerine in phosphate-buffered saline, and then covered with a round coverslip and sealed. The slides were analyzed using a Nikon Lab Diaphot fluorescent microscope (NiKon Inc., Melville, N.Y.) and photographed using TRI X Pan 400 ASA Kodak film).

Identification of Albumin-Binding Proteins

Plasma membranes were first isolated from BPMVEC by differential centrifugation and the albumin-binding proteins present in this membrane fraction were identified using ligand blotting (see above). A simple method was developed, to identify native albumin-binding proteins in endothelial cell membranes. The membrane proteins were separated using SDS-PAGE and then transferred to PVDF or nitrocellulose. Non-specific binding was blocked by incubating the membrane strips with Tween-20, and then treated with globulin-free monomeric native BSA. The BSA-binding regions were identified using polyclonal antibody raised against native BSA. In the absence of exposure of the membrane strip to native BSA, the anti-BSA recognized only a 67 kDa polypeptide, indicating the presence of a significant amount of BSA bound to endothelial cell membranes. However, when the strip was treated with BSA, the anti-BSA antibody reacted with 3 additional polypeptides (110 kDa, 57 kDa and 18 kDa). Of these polypeptides, the antibody reacted most intensely with 57 kDa, indicating the 57 kDa polypeptide to be the major native albumin-binding protein. Total endothelial cell membrane fractions (100,000×g particulate fraction from BPMVEC and BPAEC) were also prepared and used for ligand blotting. These particulate fractions also showed a primary interaction of BSA with the 57 kDa polypeptide.

Isolation of the 57 kDa Albumin-Binding Protein

Since binding of native albumin was seen primarily with the 57 kDa protein, a method was developed for the isolation of this protein from BPMVEC membranes. Ligand blotting was employed to assess the presence of this protein during purification. BPMVEC membranes were initially solubilized with 2.5% sodium cholate and 4M urea, and the extract was dialyzed and concentrated by 60% ethanol precipitation. This precipitate was re-extracted with Triton x-100 (see above). The Triton x-100 solubilized extract was chromatographed on the DEAE column, and the bound proteins were eluted with linear gradient (0–500 mM NaCl). The proteins were eluted as 3 peaks. The fractions from each peak were pooled and screened for albumin-binding using the ligand blotting assay. Only one peak (I) showed albumin-binding with the 57 kDa protein region.

SDS electrophoresis was conducted, using proteins from native BPMVEC membrane and DEAE column peak I after staining with Coomassie brilliant blue R-250. The presence of 57 kDa protein corresponding to albumin-binding was observed with ligand blotting in both native membranes as well as in DEAE peak I. SDS-PAGE was also performed under non-reducing conditions (in absence of βME), and the albumin-binding was observed only with 57 kDa region, suggesting the absence of sulfide link in this protein. This protein was further purified using preparative SDS-PAGE, and the protein eluted from gel was used for the antibody preparation.

Immunoblotting

BPMVEC and BPAEC membrane proteins were separated by using SDS-PAGE and transferred to nitrocellulose strips. The strips were immunoblotted with the 57 kDa antiserum. The preimmune serum did not recognize any proteins from BPMVEC and BPAEC membranes. The antiserum recognized two major proteins (57 kDa and 36 kDa) and one minor protein (43 kDa) in both membrane preparations. The particulate fractions from BPMVEC and BPAEC were also used for immunoblotting. The antibody recognized only these three proteins in the particulate fractions. This suggests that the albumin-binding protein was purified to an apparent homogeneity.

To study the proposed structural relationship between the endothelial membrane-associated and secreted (SPARC) albumin-binding proteins, immunoblotting of BPMVEC membranes was carried out with the antibodies raised against purified bovine SPARC. The antiserum raised against purified bovine SPARC recognized 67 kDa, 61 kDa, 57 kDa, 43 kDa and 36 kDa polypeptides in BPMVEC membranes. The anti-SPARC-NH2 terminal peptide antiserum reacted strongly with a 36 kDa polypeptide and weakly with a 43 kDa polypeptide. This suggests that scavenger receptors are quite different from native albumin receptors.

Effect of Anti-57 kDa-IgG on Binding of $^{125}$I-BSA to BPMVEC Monolayers

Preimmune serum-IgG and the anti-57 kDa-IgG were affinity-purified using Protein-A Sepharose column. The influence of IgG fractions on binding of $^{125}$I-BSA to BPMVEC monolayers at 4° C. was investigated: non-specific binding ranged from 40–50%. The preimmune serum-IgG did not significantly affect the specific binding of $^{125}$I-BSA to the BPMVEC monolayers. In contrast, the anti-57 kDa-IgG reduced the specific binding of $^{125}$I-BSA to BPMVEC monolayers in a dose-dependent manner. The reduction was maximum (40–50%) at 200 μg/ml concentration in anti-57 kDa-IgG, and remained unchanged up to 1000 μg/ml.

These results demonstrate that the antibody developed against the 57 kDa protein does not fully recognize the albumin-binding domain in the receptor, or that the native albumin may interact with other binding sites on endothelial cell surface.

Activation of Transendothelial Albumin Flux by Anti-57 kDa-IRG in the Absence of Endothelial Cell Shape Change To study the effects of the anti-57 kDa-IgG on transendothelial transport of albumin, the transendothelial $^{125}$I-BSA clearance rates in BPMVEC monolayers was measured. The monolayers were preincubated with preimmune serum-IgG and anti-57 kDa-IgG for 15 minutes, 30 minutes and 60 minutes, and then the transendothelial $^{125}$I-BSA clearance rates were measured up to 60 minutes. The anti-57 kDa-IgG-induced increase in permeability was time-dependent. A 30-minute period of preincubation of anti-57 kDa-IgG resulted in a 2-fold increase in $^{125}$I-BSA clearance rate over preimmune IgG. No significant increase in permeability was seen with 15 min. preincubation, and a 40–50% change was noticed when anti-57 kDa-IgG was pre-incubated with the monolayer up to 60 min. The preimmune serum-IgG had no influence on transendothelial albumin transport at all preincubation periods tested. The anti-57 kDa-IgG effect on the permeability of $^{125}$I-albumin reverted at 4° C.

The shape change of endothelial cells after treating with preimmune serum-IgG and anti-57 kDa-IgG was studied, using a technique described previously (Phillips and Tsan, supra; Siflinger-Birnboim et al, Lab Invest. 67:24–30 (1992)). BPMVEC grown on nucleopore filters were preincubated with preimmune serum-IgG and anti-57 kDa IgG for 30 min., and the monolayers were stained with rhodamine phalloidin (see above). No cell "rounding" or formation of interendothelial gaps was observed in either case.

These results suggest that anti-57kD albumin-binding protein antibody activates albumin transport. There is another possibility, i.e. that this antibody may non-specifically increase the pericellular transport of albumin, by widening the interendothelial junctional gaps. To delineate this, the effect of anti-receptor IgG and preimmune serum IgG on endothelial cell morphology was studied. Pretreatment of BPMVEC monolayers with either preimmune serum-IgG or anti-receptor-IgG had no influence on inter-endothelial junctional gaps. This antibody to the 57 kDa albumin-binding protein may activate the transcytosis of albumin. The permeability increasing effect of this antibody did not occur at 4° C., supporting the conclusion that the antibody activated albumin transcytosis via formation of vesicles, which have been shown to be temperature-sensitive (Lo et al, J. Cell. Physiol. 151:63–70 (1992)).

EXAMPLE 2
Antibodies Raised Against GP60

Antibody raised against GP60 from endothelial cells was used to probe epithelial membrane extracts as described in Example 1. The anti-GP60 antibodies recognized a 60 kDa protein found in the epithelial extracts. This clearly shows that an immunologically-related protein is present in this system.

Epithelial and endothelial cells were grown as monolayers, as described in Example 1, to produce confluent monolayers showing the appropriate reactivity to solute flux. Anti-GP60 antibody (200–500 $\mu$g/ml) was incubated with the monolayers at 4° C. to bind antibody to the receptor, in the absence of metabolic activity that might result in internalization of the GP60. Binding of anti-GP60 antibody under these conditions resulted in a 80–90% decrease in $^{125}$I-BSA binding by the endothelial monolayers. The epithelial monolayers were further incubated with a second antibody to the primary rabbit anti-GP60 antibody, to cross-link the receptors. Both monolayers were washed and then incubated with $^{125}$I-BSA for the epithelial cells or $^{125}$I anti-BSA immunoglobulin for the endothelial monolayers at 37° C., to allow internalization of the receptor-antibody complex and co-transcytosis of the $^{125}$I-labelled tracer. Incubation with anti-GP60 antibody resulted in a 1.6–2 fold increase in uptake over the level of a pre-immune serum control. Thus, binding the GP60 receptor by an anti-GP60 antibody results in activation of the transcytosis mechanism, thereby enhancing uptake of a macromolecule in the vicinity of the invaginating membrane.

EXAMPLE 3
Use of Albumin with Macromolecules

Endothelial monolayers were incubated at 4° C. in the presence of BSA, to initiate the binding of BSA to GP60 but to prevent the internalization of the ligand receptor complex. After extensive washing to remove unbound BSA, the cells were incubated with $^{125}$I-labelled anti-BSA immunoglobulin at 37° C., as the macromolecular tracer. Pre-treatment with BSA enhanced transcytosis of the immunoglobulin tracer by 1.5 fold over the control cells pre-incubated with unlabelled anti-BSA immunoglobulin. Further, when the cells incubated at 37° C. were washed and immediately taken through the same protocol, no macromolecular flux was observed; this shows that, once internalized, the GP60 receptor is unavailable for ligand binding. Thus, large (150 kDa) molecules can be co-transcytosed in concert with HSA using the GP60 system.

EXAMPLE 4
Use of Albumin with Peptides

Human and rat epithelial monolayers were grown to confluence, as described in Example 1. The cells were then incubated with FITC-insulin (1 mg/ml) or FITC-insulin and BSA (each 1 mg/ml) at 37° C. in the transcellular flux system described above. For human and rat epithelial monolayers, there was a 2.5 or 4 fold increase in FITC-insulin flux over the control of FITC-insulin alone. Thus, albumin also stimulates co-transcytosis of small molecular weight peptides across epithelial cells containing the GP60 receptor.

EXAMPLE 5
Use of N-Terminal Peptide 1–18 of GP60

A synthetic N-terminal peptide (T3118) of GP60 corresponding to the first 18 residues was produced by solid-phase peptide synthesis. The sequence (SEQ ID No. 1) shows at least 80% homology with the bovine, membrane-bound thyroid hormone (T3)-binding protein (Yamauchi et al, Biochem. Biophys. Res. Comm. 146:1485 (1987)). It has 97% homology with PDI.

Antibodies were raised in rabbits against T3118, and used to probe endothelial membrane extracts, to determine cross-reactivity with proteins recognized by anti-GP60 antibodies as described below. BPMVEC membrane proteins (100 $\mu$g) were separated on SDS-PAGE and transferred to nitroulose membrane strips. Non-specific binding was blocked with 5% non-fat dry milk in Tris-buffered saline. The antisera were diluted in blocking solution, incubated for 4–5 hrs at 4° C., washed and treated with goat-anti-rabbit-IgG conjugated with alkaline phosphatase. The protein bands were identified using known molecular weight marker proteins. The anti-T3118 antibodies showed only reactivity towards the GP60 protein and not towards the SPARC peptides recognized by the anti-GP60 antibody.

The T3118 peptide was then used in an endothelial uptake experiment to determine if it would act as an antagonist of albumin recognition and uptake. Endothelial monolayers were incubated at 4° C. in the presence of $^{125}$I-BSA or $^{125}$I-BSA plus the T3118 peptide. After incubation, the cells were washed extensively, lysed and counted for tracer uptake. Surprisingly, rather than acting as an antagonist, the T3118 peptide actually stimulated uptake of albumin 5-fold over the albumin alone control. The enhancement was saturable at a concentration of 500 $\mu$m of T3118 peptide. These data suggest that the T3118 peptide, acting as an agonist, may induce a conformational change in albumin, which enhances recognition by GP60, or is the signal for uptake by the endothelial cells.

It will be appreciated by those skilled in the art that the invention can be performed within a wide range of equivalent parameters of composition, concentrations, modes of administration, and conditions without departing from the spirit or scope of the invention or any embodiment thereof.

What is claimed is:

1. A composition comprising, or conjugate of, a physiologically-active agent that exerts its action following passage across endothelia, epithelia or mesothelia containing the GP60 receptor, and a transcytosis enhancer or vehicle selected from albumin and fragments thereof, anti-GP60 antibody and fragments thereof, GP60 peptide fragments, and PDI (protein disulphide isomerase) and fragments thereof; wherein said composition or conjugate is a dry powder suitable for inhalation.

2. The composition or conjugate according to claim 1, wherein the transcytosis enhancer or vehicle includes the CGMC motif.

3. The composition or conjugate according to claim 1, wherein the transcytosis enhancer or vehicle comprises albumin or an albumin fragment.

4. The composition or conjugate according to claim 1, wherein the transcytosis enhancer or vehicle comprises anti-GP60 antibody or an anti-GP60 antibody fragment.

5. The composition or conjugate according to claim 1, wherein the transcytosis enhancer or vehicle comprises a GP60 peptide fragment.

6. The composition or conjugate according to claim 1, wherein the transcytosis vehicle comprises albumin or an albumin fragment in combination with a GP60 peptide fragment.

7. The composition or conjugate according to claim 5 or claim 6, wherein the GP60 peptide fragment is or comprises SEQ ID No. 1.

8. The composition or conjugate according to claim 1, wherein the physiologically-active agent is selected from the group consisting of Luteinizing hormone (LH), chorionic gonadotropin, atrial peptides, interferon, lymphokines I, lymphokine II, lymphokine III, lymphokine IV, lymphokine V, lymphokine VI, lymphokine VII, a colony-stimulating factor, growth hormone-releasing factor, corticotropin-releasing factor, luteinizing hormone-releasing hormone (LHRH), somatostatin, calcitonin, thyrotropin-releasing hormone, calcitonin gene-related peptide (CGRP), transferases, hydrolases, isomerases, proteases, ligases, oxidoreductases, esterases, phosphatases, nerve growth factor (NGF), ciliary neurotrophic factor (CNTF), brain-derived neurotrophic factor (BDNF), glial-derived neurotrophic factor (GDNF), epidermal growth factor (EGF), fibroblast growth factor (FGF), insulin-like growth factor, tumour necrosis factor (TNF), transforming growth factor (TGF), encephalins, endorphins, gonadoliberin, melanostatin, melonoliberin, somatostatin, thyroliberin, substance P, neurotensin, corticotropin, lipotropin, melanotropin, lutropin, thyrotropin, prolactin, somatotropin, neurohypophyseal hormones, parathyrin, calcitonin, thymosin, thymopoietin, circulating thymic factor, thymic humoral factor, insulin, glucagon, somatostatin, gastrin, cholecystokinin, secretin, gastric inhibitory polypeptide, vasointestinal peptide, motillin, relaxin, angiotensin, bradykinin, somatomedins, epidermal growth factors, urogastrone, deferoxamine, buserelin, deslorelin, gonadorelin, goserelin, histrelin, leuprorelin, nafarelin, and triptorelin.

9. In a method for administering a physiologically-active agent to a mammal, the improvement comprising:

administering said active agent either conjugated to or in admixture with a transcytosis vehicle or enhancer as defined in claim 1, wherein said transcytosis vehicle or enhancer delivers or enhances passage of said physiologically-active agent across epithelia, endothelia, or mesothelia containing the GP60 receptor.

10. The method of claim 9, wherein said physiologically-active agent is selected from the group consisting of Luteinizing hormone (LH), chorionic gonadotropin, atrial peptides, interferon, lymphokine I, lymphokine II, lymphokine III, lymphokine IV, lymphokine V, lymphokine VI, lymphokine VII, a colony-stimulating factor, growth hormone-releasing factor, corticotropin-releasing factor, luteinizing hormone-releasing factor (LHRH), somatostatin, calcitonin, thyrotropin-releasing hormone, calcitonin gene-related peptide (CGRP), transferases, hydrolases, isomerases, proteases, ligases, oxidoreductases, esterases, phosphatases, nerve growth factor (NGF), ciliary neurotrophic factor (CNTF), brain-derived neurotrophic factor (BDNF), glial-derived neurotrophic factor (GDNF), epidermal growth factor (EGF), fibroblast growth factor (FGF), insulin-like growth factor, tumor necrosis factor (TNF), transforming growth factor (TGF), encephalins, endorphins, gonadoliberin, melanostatin, melonoliberin, somatostatin, thyroliberin, substance P, neurostensin, corticotropin, lipotropin, melanotropin, lutropin, thyrotropin, prolactin, somatotropin, neurohypophyseal hormones, parathyrin, calcitonin, thymosin, thymopoietin, circulating thymic factor, thymic humoral factor, insulin, glucagon, somatostatin, gastrin, cholecystokinin, secretin, gastric inhibitory polypeptide, vasointestinal peptide, motillin, relaxin, angiotensin, bradykinin, somatomedins, epidermal growth factors, urogastrone, deferoxamine, buserelin, deslorelin, gonadorelin, goserelin, histrelin leuprorelin, nafarelin, and triptorelin.

11. The method of claim 9, wherein said physiologically-active agent is conjugated to said transcytosis vehicle by a method selected from the group consisting of glutaraldehyde conjugation using Schiff base formation, carbodiimide reaction between proteins and carboxylic acids, acid anhydride activation of amine containing drugs followed by carbodiimide linkage, activation of primary amine containing drugs with 3-(2-pyridyldithio)proprionate-N-succinimidyl anhydride followed by coupling to cysteine groups of proteins, coupling of sugar alcohols to proteins utilizing cyanuric chloride, and conjugation between amines and hydroxyl groups via bisperoxidation.

12. The method of claim 9, wherein said mammal is human.

13. The composition or conjugate, according to claim 1, which further comprises an excipient.

14. The composition or conjugate, according to claim 1, which comprises microparticles of the active agent which are from 2 to 5 $\mu$m in size.

15. An inhaler device which comprises a composition comprising, or conjugate of, a physiologically-active agent that exerts its action following passage across endothelia, epithelia or mesothelia containing the GP60 receptor, and a transcytosis enhancer or vehicle selected from albumin and fragments thereof, anti-GP60 antibody and fragments thereof, GP60 peptide fragments, and PDI (protein disulphide isomerase) and fragments thereof; wherein said composition or conjugate is a dry powder suitable for inhalation.

* * * * *

UNITED STATES PATENT AND TRADEMARK OFFICE
CERTIFICATE OF CORRECTION

PATENT NO. : 6,204,054 B1
DATED : March 20, 2001
INVENTOR(S) : Sutton *et al.*

It is certified that error appears in the above-identified patent and that said Letters Patent is hereby corrected as shown below:

Title page, column 1,
Lines 1-2, "TRANSCYTOSIS VEHICLES AND ENCHANCERS FOR DRUG DELIVERY" should read -- TRANSCYTOSIS VEHICLES AND ENHANCERS FOR DRUG DELIVERY --.

Column 20,
Line 66, (claim 10), "histrelin leuprorelin," should read -- histrelin, leuporelin, --.

Signed and Sealed this

Sixteenth Day of October, 2001

Attest:

NICHOLAS P. GODICI
*Attesting Officer*  *Acting Director of the United States Patent and Trademark Office*

SEQUENCE LISTING

<160> NUMBER OF SEQ ID NOS: 1

<210> SEQ ID NO 1
<211> LENGTH: 18
<212> TYPE: PRT
<213> ORGANISM: Unknown
<220> FEATURE:
<223> OTHER INFORMATION: Description of Unknown Organism: GP60 peptide

<400> SEQUENCE: 1

Lys Pro Asp Glu Glu Asp His Val Leu Val Leu Val Lys Gly Asn Phe
 1               5                  10                  15

Asp Val